United States Patent [19]

Hung

[11] Patent Number: 4,549,192

[45] Date of Patent: Oct. 22, 1985

[54] ELECTROCHROMIC MARKING SYSTEMS

[75] Inventor: William M. Hung, Cincinnati, Ohio

[73] Assignee: The Hilton-Davis Chemical Co., Cincinnati, Ohio

[21] Appl. No.: 636,471

[22] Filed: Jul. 31, 1984

[51] Int. Cl.$^4$ .............................................. B41M 5/20
[52] U.S. Cl. ...................................... 346/218; 204/2; 346/217; 427/151
[58] Field of Search ................ 346/217, 218; 427/150, 427/151; 204/2; 544/63

[56] References Cited

U.S. PATENT DOCUMENTS 3,873,340  3/1975  Miyazawa et al. ................. 346/218
3,900,217  8/1975  Hayashi et al. ..................... 346/218

FOREIGN PATENT DOCUMENTS 46-35704  10/1971  Japan .................................... 346/218
51-81629   7/1976  Japan .................................... 346/218
6104094    8/1981  Japan .................................... 346/218

*Primary Examiner*—Bruce H. Hess
*Attorney, Agent, or Firm*—Terrence E. Miesle; B. Woodrow Wyatt

[57] ABSTRACT 4-(N-Acylamino)-8-(N—R$^1$—N—R$^2$-amino)imidazophenoxazines useful as color formers, particularly in electrochromic recording systems, are prepared by the interaction of the corresponding 1,3-diamino-7-(N—R$^1$—N—R$^2$-amino)phenoxazinium halide with a reducing agent to obtain the corresponding leuco compound and subsequently interacting the leuco compound with at least two molecular proportions of an acylating agent.

6 Claims, No Drawings

ELECTROCHROMIC MARKING SYSTEMS

BACKGROUND OF THE INVENTION (a) Field of the Invention

This invention relates to novel compounds classified in the field of organic chemistry as imidazophenoxazines, useful as color-forming substances, particularly in the art of electrochromic recording; to electrochromic recording systems containing said compounds; and to processes for preparing said compounds.

(b) Information Disclosure Statement

Several classes of organic compounds of widely diverse structural types are known to be useful as colorless precursors for electrochromic recording. Among the more important classes, there may be named leuco-type dyestuffs such as: phthalides, for example, crystal violet lactone, Malachite green lactone; fluorans, for example, 3-diethylamino-5,7-dimethylfluoran; and indolinobenzospiropyrans, for example, 1,3,3-trimethyl-6'-chloro-8'-methoxyindolinobenzospiropyrans. Also utilized as colorless precursors for electrochromic recording, either alone or in admixture with the leuco compounds indicated above, are substances known as redox indicators. The redox indicator which becomes colored in situ in the electrochromic recording process also is generally a leuco compound. Among the types of compounds which are applicable as redox indicators are phenothiazines, for example, leuco methylene blue and benzoyl leuco methylene blue. Other specific indicators are Leucoethyl Nile Blue, Leucomethyl Capryl Blue and Leucosafranine T. Typical of the many such electrochromic recording systems taught in the prior art are those described in U.S. Pat. Nos. 3,726,769, 3,871,972, 3,864,684, 4,017,366, 4,133,933, and Reissue Patent Re. No. 29,427 which issued Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. Basically, a sheet of paper is coated or treated on one or both sides with a coating formulation containing at least one colorless color-forming (leuco) compound. Electrical current is then selectively applied to the coated side of the paper by some means, for example, a stylus or a printing head to which an electrical potential can be applied. The application of the current causes an electrochromic reaction involving the leuco compound to produce a visible image corresponding to the design traced by the stylus or that of the printing head.

The following items to date appear to constitute the most relevant prior art with regard to the instant invention.

U.S. Pat. No. 2,909,520, issued Oct. 20, 1959, discloses compounds having the formula

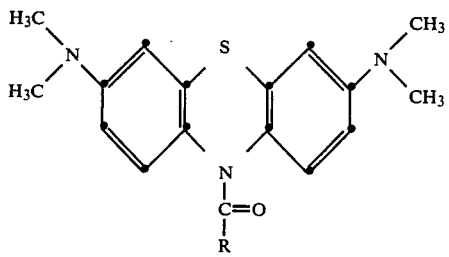

in which R is a phenyl or naphthyl group substituted with one or more of the following moieties: alkyl, alkoxy, halo, nitro, haloalkyl, alkoxycarbonyl, phenyl, and phenylalkoxy. These compounds are disclosed as being useful as blue color formers in carbonless carbon papers, i.e., carbonless duplicating systems.

Mariga and Oda in Kogyo Kagaku Zasshi 67 (7), 1050-4 (1964) (C.A. 62 2852b) describe the preparation and properties of acylated methylene blue having the structural formula

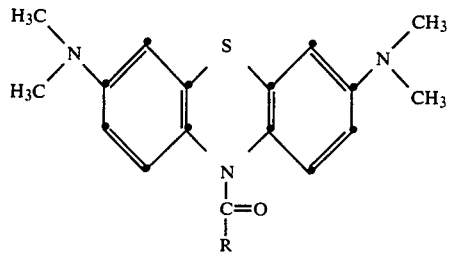

in which R represents an alkyl or a substituted phenyl moiety. The compounds are disclosed as being useful in pressure-sensitive carbonless duplicating systems.

U.S. Pat. No. 4,309,255, issued Jan. 5, 1982, discloses and claims a phenothiazine having the structural formula

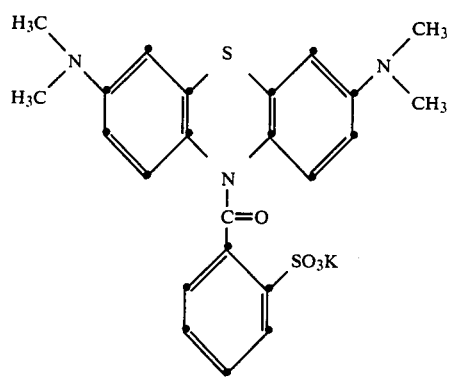

which is disclosed as being useful as a blue color former in electrochromic recording paper.

SUMMARY OF THE INVENTION

In its composition of matter aspect, the invention relates to certain 4-N-acylamino)-8-(N—R$^1$—N—R$^2$-amino)imidazophenoxazines useful as colorless precursors in electrochromic recording systems.

The present invention provides in its article of manufacture aspect, a substrate for use in electrochromic recording systems comprising a support sheet containing as a color-forming substance 4-(N-acylamino)-8-(N—R$^1$—N—R$^2$-amino)imidazophenoxazines.

In its process aspect, the invention relates to a process for producing 4-(N-acylamino)-8-(N—R$^1$—N—R$^2$-amino)imidazophenoxazines which comprises interacting the corresponding 1,3-diamino-7-(N—R$^1$—N—R$^2$-amino)phenoxazinium halide with a reducing agent to obtain the corresponding leuco compound and subsequently interacting the leuco compound with about two molecular proportions of an acylating agent.

DETAILED DESCRIPTION INCLUSIVE OF THE PREFERRED EMBODIMENTS

More specifically, this invention in its composition of matter aspect resides in the novel compounds having the structural formula

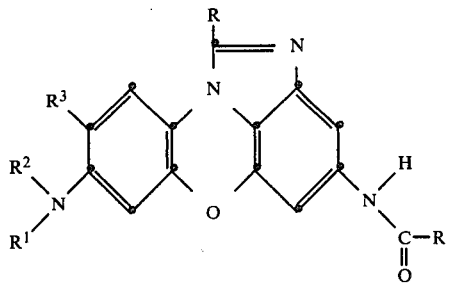

Formula I wherein R represents non-tertiary $C_1$ to $C_{12}$ alkyl, $C_4$ to $C_8$ cycloalkyl, non-tertiary $C_1$ to $C_{12}$ alkyl substituted by halogen, non-tertiary $C_1$ to $C_4$ alkoxy or non-tertiary $C_1$ to $C_4$ alkoxycarbonyl, phenyl or phenyl substituted by one to three of non-tertiary $C_1$ to $C_4$ alkyl, non-tertiary $C_1$ to $C_4$ alkoxy, nitro, halo, phenyl, cyano or trihalomethyl; $R^1$ and $R^2$ independently represent non-tertiary $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; and $R^3$ represents hydrogen or non-tertiary $C_1$ to $C_4$ alkyl.

Preferred compounds within the ambit of the composition of matter aspect are the novel 1-R-4-(N—R—CO)amino-8-(dialkylamino)-9-$R^3$-imidazophenoxazines of Formula I wherein $R^1$ and $R^2$ represent $C_1$ to $C_4$ alkyl.

In its process aspect, the invention sought to be patented resides in the process for preparing a compound according to Formula I which comprises in the first step interacting a compound having the structural formula

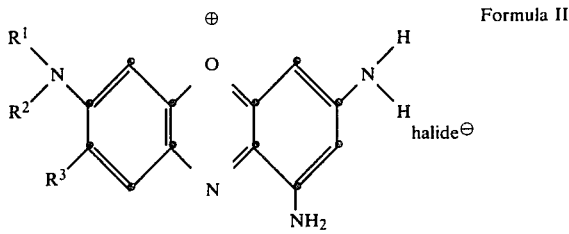

Formula II with a reducing agent to obtain the corresponding leuco compound having the structural formula

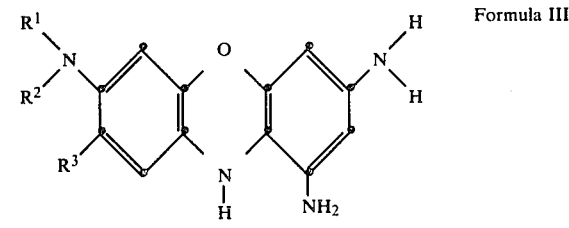

Formula III and in a second step, interacting the leuco compound with at least two molecular proportions of an anhydride of an acylating agent having the structural formula R—CO—Z  Formula IV in which Z represents halo or RCOO, and R, $R^1$, $R^2$ and $R^3$ have the same respective meanings given in Formula I.

In its article of manufacture aspect, the invention sought to be patented resides in a substrate for use in electrochromic recording comprising a support sheet containing as a color-forming substance a 1-R-3-(N—R—CO)amino-8-(N—$R^1$—N—$R^2$-amino)-9-$R^3$-imidazophenoxazine having the structure of Formula I.

A preferred embodiment within the ambit of the article of manufacture aspect is the substrate for use in electrochromic recording comprising a support sheet containing as a color-forming substance a 1—R—3—(-N—R—CO)amino-8-dialkylamino-9-$R^3$-imidazophenoxazine of Formula I wherein $R^1$ and $R^2$ are non-tertiary $C_1$ to $C_4$ alkyl.

As used herein the terms "non-tertiary $C_1$ to $C_4$ alkyl" and "non-tertiary $C_1$ to $C_{12}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl and the like.

The term "non-tertiary $C_1$ to $C_4$ alkoxy" includes saturated acyclic, straight or branched-chained groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

As used herein the term "$C_4$ to $C_8$ cycloalkyl" denotes saturated monovalent cyclic aliphatic hydrocarbon radicals including cyclobutyl, cyclopentyl, cyclohexyl, cycloheptyl, cyclooctyl and the like.

The phenoxaziniums which are used as intermediates or starting materials for the compounds of Formula I are generally known compounds readily prepared by procedures well known in the art. References to the preparation of the phenoxazines are: British Pat. Nos. 1,390/92 and 21,154/92; French Pat. No. 224,047; and German Pat. Nos. 74,918, 75,234 and 75,243.

The acylating agents of Formula IV may be either aliphatic acid anhydrides or the acid halides (Z=halo, preferably chloro) and constitute well known classes of compounds many of which are commercially-available or are readily obtained by conventional synthesis well known in the art. The following list exemplifies aliphatic acid anhydrides and acid halides useful in carrying out the processes of this invention. Acetic anhydride, chloroacetic anhydride, dichloroacetic anhydride, trifluoroacetic anhydride, propionic anhydride, butyric anhydride, isobutyric anhydride, valeric anhydride, hexanoic anhydride, hepanoic anhydride, acetyl bromide, acetyl chloride, acetyl fluoride, bromoacetyl bromide, bromoacetyl chloride, chloroacetyl chloride, methoxyacetyl chloride, propionyl chloride, 2-bromopropionyl chloride, 3-bromopropionyl chloride, 2-chloropropionyl chloride, 3-chloropropionyl chloride, butyryl chloride, 4-chlorobutyryl chloride, 2-ethylbutyryl chloride, isobutyryl chloride, valeryl chloride, 5-chlorovaleryl chloride, isovaleryl chloride, 4-methylvaleryl chloride, hexanoyl chloride, 6-bromohexanoyl chloride, heptanoyl chloride, octanoyl chloride, nonanoyl chloride, decanoyl chloride, 10-undecanoyl chloride, palmitoyl chloride, myristoyl chloride, lauroyl chloride, cyclopropyl carboxylic acid chloride, cyclobutane carboxylic acid chloride, cyclohexyl carboxylic acid chloride, m-anisoyl chloride, p-anisoyl chloride, benzoyl bromide, benzoyl chloride, benzoyl fluoride, 4-biphenylcarbonyl chloride, 2-bromobenzoyl chloride, 4-bromobenzoyl chloride, 4-butoxybenzoyl chloride, 4-butylbenzoyl chloride, 2-chlorobenzoyl chloride, 3-chlorobenzoyl chloride, 4-chlorobenzoyl chloride, 4-cyanobenzoyl chloride, 2,4-dichlorobenzoyl chloride, 2,6-dichlorobenzoyl chloride, 3,4-dichlorobenzoyl chloride, 3,5-dimethoxybenzoyl chloride, 3,4-dimethoxybenzoyl chloride, 3,5-dinitrobenzoyl chloride, 2-fluorobenzoyl chloride, 3-fluorobenzoyl chloride, 4-fluorobenzoyl chloride, 3-nitrobenzoyl chloride, 4-nitrobenzoyl chloride, 2-methoxybenzoyl chloride, 3-methylbenzoyl chloride, 4-methylbenzoyl chloride, 2-iodobenzoyl chloride, 4-iodobenzoyl chloride and 4-trifluoromethylbenzoyl chloride.

The compounds of Formula I hereinabove are essentially colorless in the depicted form. When contacted with an electric current from an applied voltage stylus of the type ordinarily employed in electrochromic recording systems, the compounds of Formula I develop purple-colored images. These developed images are very insensitive to light, that is, once the color is developed, it remains unchanged when subjected to light exposure. The developed images also possess excellent xerographic reproducibility.

The compounds of this invention may be incorporated in any of the commercially-accepted systems known in the electrochromic recording art. Typical techniques for the application of the color formers to paper are well known and are described in numerous patents, for example, U.S. Pat. Re. Nos. 29,427; 3,726,769; 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionallly in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkaline metal or alkaline earth metal salt, for example, potassium chloride, calcium chloride, sodium chloride, sodium bromide, potassium, bromide, potassium nitrate or sodium sulfate immediately prior to the printing with the applied voltage stylus. For a quick qualitative test, it has been determined that the color-forming component can be dissolved in a suitable volatile organic solvent, coated on paper and the coated paper dried to obtain a paper sheet coated with the color-forming component. This coated sheet can then be wet with a conductive salt solution and an image traced with an applied voltage stylus to develop the colored image.

The compounds of Formula I can be used alone as color-forming components in electrochromic recording paper or can be used in admixture with one or more other color-forming compounds from the classes consisting of phthalides, for example, Crystal Violet Lactone; fluorans, for example, 3-diethylamino-5,7-dimethylfluoran; redox indicators, for example, phenothiazines such as benzoyl leuco methylene blue and various other types of color-forming components currently employed in commercially-accepted electrochromic recording systems.

The best mode contemplated by the inventors of carrying out this invention will now be described so as to enable any person skilled in the art to which it pertains to make and use the same.

In accordance with the aforementioned process aspect of this invention, the compounds of Formula I may be obtained by reacting one molecular proportion of a leuco compound of Formula III with at least two molecular proportions of an aliphatic acid anhydride acylating agent of Formula IV. When an anhydride is used as the acylating agent, the reaction is conveniently carried out in an excess of the acylating agent which is utilized as both the reaction medium and as the reactant. Optionally a small amount of an organic base, for example, pyridine may be used as a catalyst. The reaction is conveniently carried out at a temperature in the range of 90° C. to reflux of the mixture for periods of approximately thirty minutes to approximately four hours. The compounds of Formula I thus obtained are isolated by pouring the reaction mixture into ice water and extracting the desired products into a suitable water immiscible organic liquid, for example, toluene. The organic liquid layer containing the product is subsequently washed with water to remove inorganic salts and water-soluble organics and then treated with decolorizing charcoal, if desired. The resulting organic liquid solution of the product is then concentrated by conventional means such as evaporation or distillation. Alternatively, the compounds of Formula I are obtained also by reacting one molecular proportion of a leuco compound of Formula III with at least two molecular proportions of an acyl halide (Formula IV, Z=halo). The leuco compound prepared as described below dissolved in an organic liquid, for example, toluene is cooled to a temperature in the range of 60° to 80° C. and disodium phosphate and R-carbonyl halide, dissolved in the same organic liquid, is added. The reaction is conveniently carried out at the reflux temperature of the mixture for periods of approximately fifteen minutes to approximately nineteen hours. Water and additional disodium phosphate are added to the reaction mixture and the resulting mixture is heated at reflux temperature for a period of approximately thirty minutes to approximately one hour. The organic liquid solution containing the desired product is separated from the water layer, washed with water and concentrated by conventional means such as evaporation or distillation. The isolated product can be purified by conventional means such as recrystallization or reslurrying with a suitable organic liquid and then collected by filtration. Another method of purification is to subject the product needing purification to separation by column chromatography. The material to be purified is dissolved in a suitable organic liquid and the solution is passed through a chromatography column which has been packed with a suitable substrate, for example, silica gel, cellulose and alumina. Numerous fractions are collected and analyzed to determine fraction(s) containing the desired product. The fraction(s) which contain the desired product are then combined (if more than one) and concentrated to obtain the product.

The leuco compound of Formula III is conveniently prepared by reducing the corresponding phenoxazinium halide of Formula II with a reducing agent, for example, zinc dust or sodium hydrosulfite. When zinc dust is used as the reducing agent, the reaction is conveniently carried out in an excess of an anhydride acylating agent, thus eliminating the need for an inert organic liquid reaction medium. When using hydrosulfite as the reducing agent, the reaction in which the leuco compound is prepared is conveniently carried out in a mixture of water and a suitable water immiscible organic liquid, for example, toluene or xylene in an inert atmosphere, for example, nitrogen. The reaction is carried out in the presence of an alkaline substance, for example, sodium carbonate or disodium phosphate using, as the reducing agent, an alkali hydrosulfite, for example, sodium hydrosulfite. The reaction is conveniently carried out at ambient temperature for a period of approximately fifteen minutes to approximately two hours. The organic liquid solution which contains the leuco compound is separated from the water layer. Additional alkali hydrosulfite is added to the organic liquid solution and the resulting mixture is azeotroped to remove the remaining traces of water and then used directly in the acylating step as described hereinabove.

The molecular structures of the compounds were assigned on the basis of the modes of synthesis and a study of their infrared, nuclear magnetic resonance and mass spectra.

The following examples will further illustrate the invention without, however, limiting thereto.

EXAMPLE 1

A mixture of 10.0 g of 1,3-diamino-7-diethylamino-8-methylphenoxazin-5-ium chloride (Brilliant Cresyl Blue, Eastman Kodak), 50.0 ml of acetic anhydride, 10.0 g of zinc dust and 10.0 ml of pyridine was maintained at 85° to 90° C. for approximately one hour. After cooling to room temperature, the reaction mixture was poured into a mixture of water and toluene and the resulting water layer was separated and discarded. The toluene solution was washed twice, first with water and then with saturated sodium chloride solution. The toluene was removed by evaporation at reduced pressure. The resulting residue was recrystallized from isopropanol and the solid obtained was recrystallized from ethanol to obtain 0.2 g of 1,9-dimethyl-4-acetamido-8-diethylaminoimidazophenoxazine (Formula I: $R=R^3=CH_3$; $R^1=R^2=C_2H_5$), a white solid which melted at 217° to 218° C. A significant infrared maximum appeared at 1660 cm$^{-1}$ (C=O;s). The nuclear magnetic resonance spectrum was consistent with the assigned structure. Paper coated with an ink formulation of the product produced a purple-colored image when contacted with an applied voltage stylus.

EXAMPLE 2

Under a nitrogen atmosphere, a mixture of 10.0 g of 1,3-diamino-7-diethylamino-8-methylphenoxazin-5-ium chloride, 400.0 ml of water, 400.0 ml of toluene, 15.0 g of sodium carbonate and 20.0 g of sodium hydrosulfite was stirred for approximately two hours at room temperature and the water layer was separated and discarded. To the toluene solution, 10.0 g of sodium hydrosulfite was added and the resulting mixture was dried by azeotroping off the remaining traces of water. After cooling to room temperature, 25.0 ml of paraanisoyl chloride was added and the mixture was maintained at reflux for approximately two hours. After cooling to room temperature, the reaction mixture was poured into water. The toluene solution and water mixture was filtered to remove some solid present which was later determined not to be the desired product. The water layer was separated and discarded. The toluene layer was washed five times as follows: twice, each time with 800.0 ml of water; once with 800.0 ml of aqueous saturated sodium carbonate solution; once with 800.0 ml of water; and once with 800.0 ml of saturated aqueous sodium chloride solution. The toluene solution was then evaporated to dryness under reduced pressure. The residue was reslurried in a small amount of fresh toluene and the solid collected by filtration, washed three times, each with 25.0 ml of toluene, and dried to obtain 3.76 g of 1-(4-methoxyphenyl)-4-(4-methoxybenzamido)-8-diethylamino-9-methylimidazophenoxazine (Formula I: $R=4-CH_3OC_6H_4$; $R^1=R^2=C_2H_5$; $R^3=CH_3$), a pale gray-colored solid which melted at 189° to 192° C. A significant infrared maximum appeared at 1678 cm$^{-1}$ (C=O;s). Paper coated with an ink formulation containing the product produced a purple-colored image when contacted with an applied voltage stylus.

EXAMPLE 4

Proceeding in a manner similar to that described in Example 1 above, a mixture of 5.42 g of 1,3-diamino-7-diethylamino-8-methylphenoxazine, 3.0 g of zinc dust, 5.0 ml of pyridine and 50.0 ml of butyric anhydride was interacted to obtain, after recrystallization from acetone, 2.23 g of 1-propyl-4-butyramido-8-diethylamino-9-methylimidazophenoxazine (Formula I: $R=C_3H_7$; $R^1=R^2=C_2H_5$; $R^3=CH_3$), a white powder which melted at 162° to 163° C. A significant infrared maximum appeared at 1678 cm$^{-1}$ (C=O;s). Paper coated with an ink formulation containing the product produced a purple-colored image when contacted with an applied voltage stylus.

It is contemplated that by following the procedure described in the foregoing examples, but employing the appropriate 1,3-diamino-7-(N-R$^1$-N-R$^2$-amino)-8-R$^3$-phenoxazinium halide of Formula II with a reducing agent and the appropriate acylating agent of Formula IV, there will be obtained 1—R—3-(N-R-CO)amino-8-(N—R$^1$—N—R$^2$-amino)-9—R$^3$-imidazophenoxazine of Formula I, presented in Examples 5 to 23 in Table A hereinbelow.

TABLE A

| Example No. | R | R$^1$ | R$^2$ | R$^3$ |
|---|---|---|---|---|
| 5 | ClCH$_2$ | C$_6$H$_5$CH$_2$ | C$_6$H$_5$CH$_2$ | H |
| 6 | CH$_3$OCH$_2$ | C$_2$H$_5$ | CH$_3$ | CH$_3$ |
| 7 | C$_3$H$_5$ | C$_6$H$_5$ | CH$_3$ | C$_2$H$_5$ |
| 8 | Cl$_2$CH | C$_4$H$_9$ | C$_4$H$_9$ | C$_4$H$_9$ |
| 9 | C$_5$H$_{11}$ | 4-CH$_3$C$_6$H$_4$CH$_2$ | 4-CH$_3$C$_6$H$_4$CH$_2$ | H |

TABLE A-continued

| Example No. | R | $R^1$ | $R^2$ | $R^3$ |
|---|---|---|---|---|
| 10 | $BrCH_2$ | $4\text{-}NO_2C_6H_4CH_2$ | $CH_3$ | $CH_3$ |
| 11 | $3\text{-}BrC_2H_4$ | $CH_3$ | $C_6H_5$ | $C_4H_9$ |
| 12 | $2\text{-}BrC_2H_4$ | $3\text{-}ClC_6H_4CH_2$ | $C_2H_5$ | $CH_3$ |
| 13 | $4\text{-}ClC_3H_7$ | $C_4H_9$ | $C_4H_9$ | $C_2H_5$ |
| 14 | $2\text{-}(C_2H_5)C_3H_7$ | $C_2H_5$ | $3\text{-}BrC_6H_4CH_2$ | $C_3H_7$ |
| 15 | $6\text{-}BrC_5H_{11}$ | $2,4\text{-}Cl_2C_6H_3CH_2$ | $CH_3$ | H |
| 16 | $C_{11}H_{23}$ | $C_2H_5$ | $2,3\text{-}(CH_3)_2C_6H_3CH_2$ | $C_2H_5$ |
| 17 | $C_3H_5$ | $2,5\text{-}(CH_3)_2C_6H_3CH_2$ | $C_2H_5$ | $CH_3$ |
| 18 | $4\text{-}C_4H_9OC_6H_4$ | $2,6\text{-}Cl_2C_6H_3CH_2$ | $CH_3$ | $C_3H_7$ |
| 19 | $4\text{-}C_4H_9C_6H_4$ | $2\text{-}FC_6H_4CH_2$ | $C_4H_9$ | $C_4H_9$ |
| 20 | $2,4\text{-}Cl_2C_6H_3$ | $2\text{-}CH_3C_6H_4CH_2$ | $2\text{-}CH_3C_6H_4CH_2$ | H |
| 21 | $3,5\text{-}(CH_3O)_2C_6H_3$ | $4\text{-}CH_3C_6H_4CH_2$ | $C_2H_5$ | $CH_3$ |
| 22 | $3,5\text{-}(NO_2)_2C_6H_3$ | $C_2H_5$ | $C_2H_5$ | $C_2H_5$ |
| 23 | $2\text{-}IC_6H_4$ | $CH_3$ | $CH_3$ | $C_4H_9$ |

What is claimed is:

1. A substrate for use in electrochromic recording comprising a support sheet containing as a color-forming substance a 1-R—4—(N—R—CO)amino-8-[N-($R^1$)($R^2$)amino]-9-$R^3$-imidoxophenoxazine having the formula

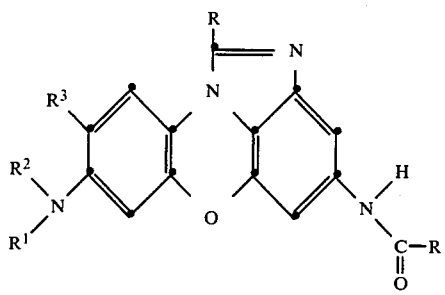

wherein:

R represents non-tertiary $C_1$ to $C_4$ alkyl, $C_4$ to $C_8$ cycloalkyl, non-tertiary $C_1$ to $C_4$ alkyl substituted with halogen, non-tertiary $C_1$ to $C_4$ alkoxy or non-tertiary $C_1$ to $C_4$ alkoxycarbonyl, phenyl or phenyl substituted by one to three of non-tertiary $C_1$ to $C_4$ alkyl, non-tertiary $C_1$ to $C_4$ alkoxy, nitro, halo, phenyl, cyano, or trihalomethyl;

$R^1$ and $R^2$ independently represent $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy; and $R^3$ and represents hydrogen or non-tertiary $C_1$ to $C_4$ alkyl.

2. A substrate for use in electrochromic recording according to claim 1 comprising a support sheet containing as a color-forming substance a 1-R-4-(N—R—CO)amino-8-dialkylamino-9-$R^3$-imidazophenoxazine.

3. A substrate for use in electrochromic recording according to claim 2 comprising a support sheet containing as a color-forming substance 1,9-dimethyl-4-acetamido-8-diethylaminoimidazophenoxazine.

4. A substrate for use in electrochromic recording according to claim 2 comprising a support sheet containing as a color-forming substance 1-(4-methoxyphenyl)-4-(4-methoxybenzamido)-8-diethylamino-9-methylimidazophenoxazine.

5. A substrate for use in electrochromic recording according to claim 2 comprising a support sheet containing as a color-forming substance 1-phenyl-4-benzamido-8-dimethylamino-9-methylimidazophenoxazine.

6. A substrate for use in electrochromic recording according to claim 2 comprising a support sheet containing as a color-forming substance 1-propyl-4-butyramido-8-diethylamino-9-methylimidazophenoxazine.

* * * * *